United States Patent [19]

Rodewald

[11] 3,976,714

[45] Aug. 24, 1976

[54] NORMAL PARAFFIN ALKYLATION WITH A CATALYST OF A LEWIS ACID AND GROUP VIII METAL INTERCALATED IN GRAPHITE

[75] Inventor: Paul G. Rodewald, Rocky Hill, N.J.

[73] Assignee: Mobil Oil Corporation, New York, N.Y.

[22] Filed: June 26, 1975

[21] Appl. No.: 590,535

Related U.S. Application Data

[62] Division of Ser. No. 467,316, May 6, 1974, Pat. No. 3,925,495.

[52] U.S. Cl.................... 260/683.47; 260/683.53
[51] Int. Cl.²........................................ C07C 3/56
[58] Field of Search................ 260/683.47, 683.48, 260/683.53, 683.68; 252/447

[56] References Cited
UNITED STATES PATENTS

| | | | |
|---|---|---|---|
| 2,342,124 | 2/1944 | Danforth | 260/683.53 |
| 3,678,120 | 7/1972 | Bloch | 260/683.47 |
| 3,708,553 | 1/1973 | Olah | 260/683.47 |
| 3,804,916 | 4/1974 | Lalancette | 252/447 |
| 3,925,495 | 12/1975 | Rodewald | 260/683.68 |

*Primary Examiner*—G. J. Crasanakis
*Attorney, Agent, or Firm*—Charles A. Huggett; Raymond W. Barclay

[57] ABSTRACT

Normal paraffin alkylation with an alkylating agent, i.e. olefin, alkylhalide or alcohol, is effected in the presence of a catalyst of graphite having intercalated in the lattice thereof between about 5 and about 75 weight percent of a Lewis acid. The catalyst utilized in alkylation has additionally intercalated therein between about 0.1 and about 20 weight percent of a Group VIII metal.

6 Claims, No Drawings

NORMAL PARAFFIN ALKYLATION WITH A CATALYST OF A LEWIS ACID AND GROUP VIII METAL INTERCALATED IN GRAPHITE

CROSS REFERENCE TO RELATED APPLICATION

This application is a division of application Ser. No. 467,316 filed May 6, 1974, now U.S. Pat. No. 3,925,495 which issued on Dec. 9, 1975.

BACKGROUND OF THE INVENTION

1. Field of the Invention

This invention relates to the conversion of hydrocarbons in the presence of a unique catalyst in which active catalytic sites are intercalated in the lattice of graphite.

2. Description of the Prior Art

It has heretofore been known to accomplish the conversion of hydrocarbons in the presence of a wide variety of catalysts including those in which the active catalytic component is deposited on a porous inert support such as, for example, graphite. U.S. Pat. No. 3,678,120 describes such process in which the catalyst employed is a porous inert solid support having deposited thereon a catalytic complex of an antimony pentafluoride component and a hydrogen fluoride or a fluorosulfonic acid component. It has been reported in U.S. Pat. No. 3,708,553 that hydrocarbon conversion and more specifically alkylation can be carried out in the presence of a catalyst of a Lewis acid such as antimony pentafluoride combined with a Bronsted acid such as fluorosulfuric acid. The intercalation of various salts in the lattice of graphite has previously been described. Thus, it has been reported in J. Chem. Soc., Chem. Comm., 21, 815(1973) that intercalation of antimony pentafluoride in the lattice of graphite is accomplished by heating a mixture of $SbF_5$ and graphite at 110°C. for a few days. In none of this prior art, which is the most relevant known, is there any recognition or disclosure of utilizing a catalyst in which active catalytic sites are intercalated within the lattice of graphite.

SUMMARY OF THE INVENTION

In accordance with the present invention, there is provided a catalytic process for converting hydrocarbons in the presence of a heterogeneous catalyst consisting essentially of graphite having intercalated therein a Lewis acid of the formula $MX_n$ where M is an element selected from Group II-A, III-A, IV-B, V or VI-B of the Periodic Table, X is a halogen and $n$ is an integer of from 2 to 6. In one embodiment of the invention, the catalyst may additionally have intercalated in the graphite a Bronsted acid such as hydrofluoric acid, hydrochloric acid, fluorosulfuric acid or trifluoromethane-sulfonic acid and mixtures thereof. In another embodiment of the invention, the graphite/intercalated Lewis acid composite may have a Group VI-B or Group VIII metal additionally intercalated in the graphite to provide a highly effective catalyst for the conversion of hydrocarbons including isomerization, polymerization, cracking and alkylation.

The graphite utilized in the present catalyst is desirably characterized by a surface area of about 0.3 to about 50 m²/gram; a typical graphite applicable for use in the present invention is characterized by the following properties:

Surface Area of 0.46 m²/gram
Real Density of 2.16 gram/cc
Particle Density of 1.90 gram/cc
Pore Volume of 0.065 cc/gram Lewis acids suitable for use in the catalysts employed in the present invention include the Group II-A, III-A, IV-B, V and VI-B halides. Representative of such compounds are vanadium pentafluoride, boron trifluoride, aluminum chloride, niobium pentafluoride, tantalum pentafluoride, ferric chloride, antimony pentafluoride, titanium tetrafluoride, bismuth pentafluoride, molybdenum hexafluoride, beryllium chloride, zirconium tetrafluoride, arsenic pentafluoride and phosphorus pentafluoride. In addition to the fluorides, the chlorides, bromides or iodides may be employed. The amount of Lewis acid intercalated in the lattice of graphite is generally between about 5 and about 75 weight percent and preferably between about 10 and about 60 weight percent.

When a Bronsted acid, such as hydrofluoric acid, hydrochloric acid, fluorosulfuric acid or trifluoromethane-sulfonic acid is also intercalated in the graphite lattice, the amount thereof is generally between about 0.5 and about 75 weight percent and preferably between about 1 and about 50 weight percent, with the molar ratio of Bronsted to Lewis acid being within the range of 0.1:1 to 50:1 and more particularly in the range of 0.1:1 to 5:1.

When a Group VI-B or Group VIII metal is additionally intercalated in the graphite, the amount employed is such as to afford a resulting composite containing between about 0.1 and about 20 weight percent of the metal. With metals of the platinum group, the amount of metal is preferably in the approximate range of 0.1 and 5 weight percent. Other metals contemplated for intercalation include nickel, cobalt, iron, chromium, molybdenum and tungsten. Particularly preferred are the Group VIII metals, especially platinum and palladium.

Intercalation of the Lewis acid in the lattice of the graphite is readily effected by heating a mixture of graphite and the Lewis acid, generally in the presence of chlorine, at a temperature between about 80° and 150°C., preferably at approximately 110°C. for a period of between about 1 and about 72 hours. When a metal of Group VI-B or Group VIII is also desired in the catalyst, intercalation is achieved by heating a compound of the appropriate metal with graphite, preferably in the presence of chlorine, at a temperature within the approximate range of 100° to 200°C. for a period of between about 4 and about 24 hours. The intercalated metal compound is then reduced, generally with flowing hydrogen, at a temperature of about 300° to about 400°C. for a period of approximately 8 to about 24 hours. Thereafter, intercalation of the desired Lewis acid into the metal/intercalated graphite composite may be effected as described above. In similar fashion, when a Bronsted acid is additionally desired in the catalyst, such acid may be intercalated after intercalation of the Lewis acid into the lattice of the graphite. Intercalation of the Bronsted acid is achieved by heating the graphite with such acid at a temperature between about −40°C. and about 100°C. for a period of between about 1 and about 5 hours. It is also feasible and, in some instances preferable, to intercalate both (1) a metal of Group VI-B or Group VIII and (2) a Bronsted acid into the lattice of the graphite having Lewis acid intercalated therein. In such embodiment, the graphite is treated to introduce the Group VI-B or Group VIII metal, as described above, followed by intercalation of the Lewis acid under the conditions specified hereinabove, and then intercalation of the Bronsted acid as described.

A wide variety of hydrocarbon conversion reactions may be effected utilizing the present catalyst. Such conversion processes include those catalyzed by the presence of acidic sites such as cracking, isomerization, alkylation, polymerization, disproportionation, dealkylation, transalkylation and similar related processes. These processes are effected by contacting a hydrocarbon or hydrocarbon mixture with the above-described catalyst at hydrocarbon conversion conditions. The catalyst to hydrocarbon weight ratio employed is generally between about 1:5 and about 1:20. The temperature employed is generally between about 0° and about 650°C. Contact between the catalyst and hydrocarbon charge may take place utilizing any of the conventional systems such as a fixed bed system, a moving bed system, a fluidized bed system or a continuous or batch-type operation. The hydrocarbon conversion utilizing the present catalyst may be carried out as either a vapor phase, a liquid phase or a mixed phase operation. Conversion may take place in the absence or presence of hydrogen. Operation in the presence of hydrogen is particularly advantageous for isomerization in preserving catalyst life.

Isomerization of isomerizable hydrocarbons, such as naphthenes and/or paraffins, may be effectively carried out utilizing the catalyst of this invention. Thus, isomerization of straight chain or slightly branched chain paraffins containing 4 or more carbon atoms per molecule, such as normal butane, normal pentane, normal hexane, normal heptane, and normal octane may be readily effected. Likewise, cycloparaffins containing at least 5 carbon atoms in the ring, such as alkyl cyclopentanes and cyclohexanes may be effectively isomerized utilizing the present catalyst. It is contemplated that straight or branched chain saturated hydrocarbons containing up to 30 carbon atoms or more per molecule may be isomerized with the present catalyst, regardless of the source of such hydrocarbons or mixtures containing the same. As examples of commercial mixtures, mention can be made of straight-run tops or light naphtha fractions which in various refineries are available in large amounts.

In carrying out isomerization of isomerizable hydrocarbons utilizing the present catalyst, contact between the catalyst and hydrocarbon charge is conducted at a temperature between about 0° and about 200°C. and preferably between about 20° and about 150°C. at a pressure between about atmospheric and about 30 atmospheres or more. The hydrocarbon charge is passed over the catalyst at a liquid hourly space velocity generally between about 0.2 and about 10 and preferably between about 0.5 and about 4. The resulting product is withdrawn from the reaction zone, separated from the reactor effluent and recovered by any suitable means such as fractional distillation. Any unreacted starting material may be recycled to form a portion of the feedstock.

The catalyst of this invention is also suitable for catalyzing hydrocarbon cracking. The hydrocarbon charge in such process may comprise one or more normal paraffins or may be a complex mixture of paraffins, naphthenes and aromatics, such as occurs in petroleum gas oil, which is the feedstock normally conducted to a commercial catalytic cracking unit. Hydrocarbon cracking utilizing the catalyst of this invention is essentially conducted at a temperature between about 400° and 650°C., a pressure of from about atmospheric to about 5 atmospheres and employing a liquid hourly space velocity of between about 0.5 and about 100.

Alkylation employing the catalyst described herein may also be effectively carried out. Thus, alkylation of an alkylatable hydrocarbon with an olefin, alkyl halide or alcohol is desirably effected in the presence of the catalyst of this invention at alkylation conditions including a temperature of about 0° to about 150°C. and a pressure of between about atmospheric and about 500 psig. The mole ratio of alkylatable hydrocarbon to alkylating agent is preferably between about 1:1 to about 10:1.

DESCRIPTION OF SPECIFIC EMBODIMENTS

The following examples will serve to illustrate the process of the invention without limiting the same:

EXAMPLE 1

A catalyst containing 42.5% of antimony pentafluoride intercalated in the lattice of graphite was prepared by drying a sample of graphite (20–65 mesh) in a vacuum oven for 2 days at 120°C. Ten grams of the dried graphite were then transferred to a 125 cc two-neck flask fitted with a mechanical stirrer and a gas bag for maintaining a slight positive pressure of nitrogen. Antimony pentafluoride (7.40 grams) was rapidly weighed into the flask under nitrogen and the flask was then flushed with dry nitrogen. The mixture was heated with occasional stirring in an oil bath at 110°C. for a period of 1–3 days. No loss in weight or pressure increase occurred, indicating complete intercalation of the antimony pentafluoride.

A reactor was packed with 4 cc of this catalyst and placed in a pressurized flow system. Dry cyclohexane containing 0.375 mole percent dissolved hydrogen was pumped at 4 cc/hour (LHSV = 1) upflow through the catalyst bed maintained at 40°C. Conversion of cyclohexane to methylcyclopentane increased gradually to 10 percent over a period of 25 hours and remained constant at 10 percent for two hours. Such corresponds to 45 percent of the equilibrium conversion to methylcyclopentane. The temperature was then raised to 50°C. The conversion rapidly increased to 19 percent methylcyclopentane (73 percent of the equilibrium conversion), remained constant at 19 percent for 14 hours and then declined slowly. The temperature was then increased to 60°C. The conversion rapidly increased to 24 percent methylcyclopentane (80 percent of the equilibrium conversion), remained constant at 24 percent for 4 hours and thereafter declined slowly to 2 percent over a period of 18 hours.

EXAMPLE 2

A catalyst containing 42.5% of antimony pentafluoride and 0.3% platinum intercalated in the lattice of graphite was prepared by adding an aqueous solution of chloroplatinic acid containing 0.136 gram of platinum to 25 grams of 20–65 mesh graphite. The water was then distilled off under vacuum. The resulting product was dried for 2 hours at 130°C. in a stream of dry nitrogen. The chloroplatinic acid was then intercalated by heating the product at 150°C. for approximately 4 hours in the presence of chlorine. The platinum was then reduced by contact with hydrogen at 450°C. for eight hours. Antimony pentafluoride was then loaded as described in Example 1 to yield a final catalyst containing 0.3 weight percent platinum and 42.5 weight percent antimony pentafluoride.

A reactor was packed with 4 cc of this catalyst. Dry n-hexane containing 1.75 mole percent dissolved hydrogen was pumped at a liquid hourly space velocity of 1 upflow through the catalyst bed maintained at 40°C. The conversion of n-hexane to products increased rapidly to 50 percent, remained constant for 3 hours and then declined slowly. The temperature was raised to 60°C. whereupon the conversion of n-hexane rapidly increased to 65 percent.

The product distribution at 4.3 hours on-stream is shown below:

Product Distribution

| Hydrocarbon | % |
|---|---|
| Propane | 0.4 |
| 2-Methylpropane | 10.2 |
| n-Butane | 2.4 |
| 2-Methylbutane | 20.2 |
| n-Pentane | 3.4 |
| 2,2-Dimethylbutane | 10.9 |
| 2,3-Dimethylbutane/ 2-Methylpentane | 19.9 |
| 3-Methylpentane | 7.8 |
| Methylcyclopentane | 0.4 |
| 2,2-Dimethylpentane | 2.5 |
| 2,4-Dimethylpentane | 0.9 |
| 2,2,3-Trimethylbutane | 0.5 |
| 3,3-Dimethylpentane | 4.9 |
| Cyclohexane | 1.9 |
| 2-Methylhexane | 4.0 |
| 2,3-Dimethylpentane | 0.1 |
| 3-Methylhexane | 0.1 |
| 3-Ethylpentane | 0.8 |
| $C_8^+$ | 8.7 |

EXAMPLE 3

A catalyst containing 42.5% $SbF_5$ but no platinum was prepared and tested for n-hexane isomerization according to Example 2. Comparison of n-hexane conversions and the ratio of isomerization to cracking at maximum conversion in the presence and absence of platinum shows a distinct advantage in having platinum present.

| Time On-Stream (Min.) | n-Hexane Conversion 0.3% | 0% Pt. | Isomerization/ Cracking Platinum 0.3% | 0% Pt. |
|---|---|---|---|---|
| 30 | 52 | 26 | | |
| 60 | 54 | 22 | 2.02 | 0.651 |
| 90 | 32 | 8 | | |
| 120 | 24 | 4 | | |

EXAMPLE 4

A catalyst containing 31% aluminum chloride and 1.5% platinum intercalated in the lattice of graphite was prepared by adding an aqueous solution of chloroplatinic acid containing 0.547 grams of platinum to 25 grams of 20–65 mesh graphite. The water was then distilled off under vacuum and the resulting product dried for two hours at 130°C. in nitrogen. The chloroplatinic acid was then intercalated by heating the product at 150°C. for about 4 hours in the presence of chlorine. The platinum was then reduced by contact with hydrogen at 450°C. for 7 hours to yield a platinum/graphite intercalation compound containing 2.1 weight percent platinum. This compound (8.63 grams), together with aluminum chloride (3.93 grams) were weighed under nitrogen into a 125 cc two-neck flask fitted with a mechanical stirrer and a gas bag for maintaining a slight positive pressure. The flask was flushed with chlorine and heated at 110°C. for 21 hours with occasional stirring. The aluminum chloride intercalated readily to yield a catalyst containing 31 weight percent aluminum chloride and 1.5 weight percent platinum.

A reactor was packed with 4 cc of the above catalyst and placed in a pressurized flow system. Dry n-hexane, saturated with hydrogen at 465 psi and containing 0.2 weight percent t-butyl chloride was pumped upflow at a liquid hourly space velocity of 2 through the catalyst bed maintained at 40°C. Isomerization, cracking and alkylation were observed. Conversion of n-hexane to products increased rapidly to 56 percent and then decreased over 100 cc to 5 percent. Cracking and alkylation decreased relative to isomerization over this interval. Increasing the temperature to 60°C. raised the conversion to 11 percent. The n-hexane feed was next saturated with hydrogen at 700 psi and the reactor temperature was raised to 80°C. The conversion increased to 15 percent. After 192 cc of n-hexane, the temperature was raised to 100°C., with a doubling of the conversion to 31 percent. Thereafter, the conversion slowly dropped to 25 percent. After 292 cc, the temperature was raised to 120°C. The conversion increased from 25 percent to 32 percent. After 388 cc, the temperature was raised to 140°C. The conversion increased from 29 to 53 percent and remained at this level until the experiment was terminated after 408 cc. Results are summarized in Table I below.

TABLE I

| Cubic Centimeters | Propane | iso-Butane | n-Butane | iso-Pentane | n-Pentane | 2,2-Dimethyl-butane | 2,3-Dimethyl-butane 2-Methyl-pentane | 3-Methyl-pentane | n-Hexane | $C_7^+$ | T°C | LHSV |
|---|---|---|---|---|---|---|---|---|---|---|---|---|
| 8 | Trace | 9.5 | 0.4 | 12.0 | 1.7 | 3.3 | 11.4 | 4.2 | 44.0 | 13.3 | 40 | 2 |
| 100 | Trace | 0.8 | Trace | 0.9 | Trace | 0.1 | 1.8 | 0.7 | 95.0 | 0.7 | 40 | 1 |
| 116 | Trace | 1.5 | 0.1 | 1.8 | 0.1 | 0.2 | 3.9 | 1.5 | 89.5 | 1.4 | 60 | 1 |
| 192 | 0.1 | 1.9 | 0.1 | 2.3 | 0.3 | 0.3 | 5.6 | 2.4 | 85.3 | 1.8 | 80 | 1 |
| 212 | 0.4 | 3.9 | 0.5 | 5.1 | 0.7 | 0.7 | 10.8 | 4.9 | 69.5 | 3.4 | 100 | 1 |
| 292 | 0.4 | 3.2 | 0.4 | 3.7 | 0.6 | 0.5 | 9.2 | 4.2 | 75.3 | 2.4 | 100 | 1 |
| 312 | 0.7 | 3.8 | 0.7 | 4.9 | 0.8 | 0.7 | 11.6 | 5.5 | 67.8 | 3.4 | 120 | 1 |
| 388 | 0.3 | 2.7 | 0.5 | 3.8 | 0.9 | 1.0 | 12.3 | 5.5 | 70.8 | 2.4 | 120 | 1 |
| 408 | 0.8 | 5.0 | 1.2 | 8.0 | 1.8 | 2.2 | 20.2 | 7.8 | 47.1 | 5.8 | 140 | 1 |

The following two examples furnish a comparison of catalysts wherein antimony pentafluoride is (1) deposited on and (2) intercalated in graphite.

EXAMPLE 5

A catalyst of antimony pentafluoride deposited on graphite was prepared by adding 5 grams of graphite to a solution of 7.50 grams of antimony pentafluoride in 25 cc of liquid $SO_2$ at −30°C. stirring for 2 hours and then filtering rapidly under dry nitrogen. The product was transferred under nitrogen to a flask and evacuated at 100 mm mercury to remove residual $SO_2$. The vacuum was broken by bleeding in dry nitrogen.

To a reactor containing 0.5 cc (0.59 gram) of the above catalyst under nitrogen was added 4 cc of cyclohexane (freshly percolated through alumina). The mixture was placed in an oil bath at 40°C. and was stirred. Aliquots of the hydrocarbon layer were taken as a function of time and analyzed by gas chromatography. The results obtained are hereinafter summarized in Table II.

EXAMPLE 6

A catalyst of antimony pentafluoride intercalated in graphite was prepared by heating 15 grams of antimony pentafluoride with 10g of (PGR 4/30/74) graphite at 110°C. for 2.7 days under nitrogen. This catalyst was tested as in Example 5 at 40°C. for cyclohexane isomerization. The results obtained are summarized below in Table II.

TABLE II

| Temp. (°C) | Time (Hr) | Effective LHSV | % Methylcyclopentane $SbF_5$ on Graphite | $SbF_5$ in Graphite |
|---|---|---|---|---|
| 40 | 2 | 4 | 0.4 | 12 |
| 40 | 4 | 2 | 0.6 | 13 |
| 40 | 24 | 0.33 | 0.9 | 13 |

As will be evident from the above results, the catalyst in which antimony pentafluoride was intercalated in the graphite was vastly superior to the catalyst in which antimony pentafluoride was deposited on the graphite.

The following two examples furnish a comparison of catalysts wherein $HSbF_5SO_3F$ is (1) deposited on and (2) intercalated in graphite.

EXAMPLE 7

A catalyst of $HSbF_5SO_3F$ deposited on graphite was prepared by adding 5 grams of graphite to a solution of $SbF_5$ (7.50 grams) and $HSO_3F$ (6.93 grams) in 25 cc of liquid $SO_2$ at −30°C. The mixture was thereafter processed and the product tested for cyclohexane isomerization as described in Example 5. The results are hereinafter summarized in Table III.

EXAMPLE 8

A catalyst of $HSbF_5SO_3F$ intercalated in graphite was prepared by adding 3 grams of $SbF_5$ intercalated in 2 grams of graphite to a solution of $HSO_3F$ (2.77 grams) in 10 cc of liquid $SO_2$ at −30°C. After stirring for 2 hours and processing under conditions described in Example 5, the product was tested for cyclohexane isomerization. The results obtained are summarized in Table III below.

TABLE III

| Temp. (°C) | Time (Hr) | Effective LHSV | % Methylcyclopentane $HSbF_5SO_3F$ on Graphite | $HSbF_5SO_3F$ in Graphite |
|---|---|---|---|---|
| 40 | 2 | 4 | 0.035 | 5.9 |
| 40 | 4 | 2 | 0.036 | 6.6 |
| 40 | 24 | 0.33 | 0.052 | 7.2 |

It will be evident from the above results that the intercalated catalyst afforded considerably higher conversion to methylcyclopentane as compared with the catalyst in which $HSbF_5SO_3F$ was deposited on the graphite.

EXAMPLE 9

A catalyst of $HSbF_5SO_3F$ and Pt both intercalated in graphite was prepared by adding 1.91 grams $SbF_5$ and 0.054 gram Pt intercalated in graphite to a solution of $HSO_3F$ (0.88 gram) in 10 cc of liquid $SO_2$ at −30°C. After stirring for 2 hours, the $SO_2$ was distilled. The product was evacuated at 100 mm Hg to remove residual $SO_2$. The vacuum was broken by bleeding in dry nitrogen.

The product was tested for cyclohexane isomerization according to Example 1. The results obtained are summarized below in Table IV.

TABLE IV

| Time On-Stream (Hrs.) | Percent Methylcyclopentane |
|---|---|
| 0 | .06 |
| 1 | 0.15 |
| 2 | 0.85 |
| 3 | 0.53 |
| 4 | 0.39 |
| 5 | 0.34 |

It is to be understood that the foregoing description is merely illustrative of preferred embodiments of the invention of which many variations may be made by those skilled in the art within the scope of the following claims without departing from the spirit thereof.

I claim:

1. A process for effecting alkylation of a normal paraffin which comprises contacting said normal paraffin under alkylation conditions with an alkylating agent selected from the group consisting of olefin, alkylhalide and alcohol with a catalyst consisting essentially of graphite having intercalated in the lattice thereof between about 5 and about 75 weight percent of a Lewis acid consisting essentially of a halide of an element of Group IIA, IIIA, IVB, V or VIB and between about 0.1 and about 20 weight percent of a Group VIII metal.

2. The process of claim 1 wherein said alkylation conditions include a temperature between about 0°C and about 150°C, a pressure between about atmospheric and about 500 psig and a mole ratio of said normal paraffin to said alkylating agent between about 1:1 and about 10:1.

3. The process of claim 1 wherein said Lewis acid is antimony pentafluoride.

4. The process of claim 1 wherein said Lewis acid is aluminum chloride.

5. The process of claim 1 wherein said Group VIII metal is platinum.

6. The process of claim 1 wherein said alkylation is carried out in the presence of hydrogen.

* * * * *